United States Patent [19]

Wolford et al.

[11] 4,092,345
[45] May 30, 1978

[54] (CYCLO)ALKYLENEDIAMMONIUM-BIS-TETRAHALOPHTHALATES

[75] Inventors: Lionel T. Wolford, Freehold; Chien Yung Lee, Kendall Park; Anderson O. Dotson, Jr., Somerset, all of N.J.

[73] Assignee: Cities Service Company, Tulsa, Okla.

[21] Appl. No.: 709,987

[22] Filed: Jul. 30, 1976

[51] Int. Cl.² .................. C07C 63/12; C09K 3/28
[52] U.S. Cl. .................. 260/501.16; 260/326 N; 252/8.1
[58] Field of Search .................. 260/501.16, 501.2

[56] References Cited

U.S. PATENT DOCUMENTS

| 3,868,388 | 2/1975 | Dotson, Jr. | 260/326 N |
| 3,873,567 | 3/1975 | Cyba | 260/326 C |
| 3,944,598 | 3/1976 | Paustian et al. | 260/501.16 |

OTHER PUBLICATIONS

Meyer et al., "Chem. Absts.", 78,158984(u), '73.
Sprung, "Chem. Absts.", 41,1124(c), 1946.
Lituineko et al., "Chem. Absts.", 58,462(h), 1963.

Primary Examiner—Robert Gerstl
Assistant Examiner—G. T. Breitenstein
Attorney, Agent, or Firm—Patricia J. Hogan

[57] ABSTRACT (Cyclo)alkylenediammonium-bis-tetrahalophthalates corresponding to the formula:

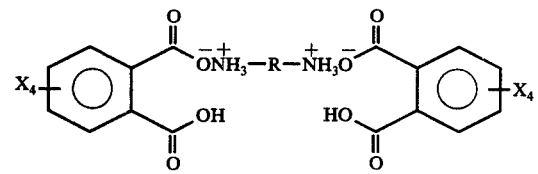

wherein X is halogen and R is an alkylene or cycloalkylene group containing 2–15 carbon atoms are prepared by hydrolyzing a tetrahalophthalic anhydride to the corresponding tetrahalophthalic acid and then reacting the tetrahalophthalic acid in the resultant reaction mixture with a diaminoalkane or diaminocycloalkane containing 2–15 carbon atoms in a molar ratio of about two molar proportions of the acid per molar proportion of the diamine.

The (cyclo)alkylenediammonium-bis-tetrahalophthalates of the invention are useful as flame retardants for normally flammable organic polymers and also have utility as intermediates for the preparation of N,N'-(cyclo)alkylene-bis-tetrahalophthalimides, which are also useful as flame retardants. The imides are prepared simply by heating the salts until an acid number of substantially 0 is obtained.

8 Claims, No Drawings

1

(CYCLO)ALKYLENEDIAMMONIUM-BIS-TETRAHALOPHTHALATES

BACKGROUND OF THE INVENTION

1. Field of the Invention

This invention relates to novel (cyclo)alkylenediammonium salts of tetrahalophthalic acids and to bisimides prepared therefrom.

2. Description of the Prior Art

As taught in U.S. Pat. No. 3,873,567 (Cyba), British Pat. No. 1,287,934 (Raychem), and Sydney M. Spatz and Herman Stone, "Some N-Substituted Tetrabromophthalimide Fire-Retardant Additives," INDUSTRIAL AND ENGINEERING CHEMISTRY PRODUCT RESEARCH AND DEVELOPMENT, Volume 8, pp. 397-398 (1969), N, N'-alkylene-bis tetrahalophthalimides having utility as flame retardants can be prepared by reacting a tetrahalophthahalic anhydride with a diaminoalkane in an organic solvent medium. These processes, which produce the bisimides via an amic acid intermediate corresponding to the formula:

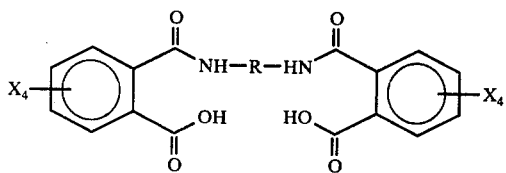

are difficult to control, present filtration problems, and are less economical than is desirable.

SUMMARY OF THE INVENTION

An object of this invention is to provide a novel process for preparing N,N'-(cyclo)alkylene-bis-tetrahalophthalimides.

Another object is to provide such a process which is economical, easily controlled, and conducive to the formation of a readily filterable product.

A further object is to provide such a process which leads to the formation of the bisimides via novel intermediates.

A still further object is to provide novel intermediates which are useful as flame retardants as well as having utility in the formation of bisimides.

These and other objects are attained by (1) hydrolyzing a tetrahalophthalic anhydride to the corresponding tetrahalophthalic acid, (2) reacting the tetrahalophthalic acid in the resultant reaction mixture with a diaminoalkane or diaminocycloalkane containing 2-15 carbon atoms in a molar ratio of about two molar proportions of the acid per molar proportion of the diamine to form an alkylene- or cycloalkylenediammonium-bis-tetrahalophthalate corresponding to the formula:

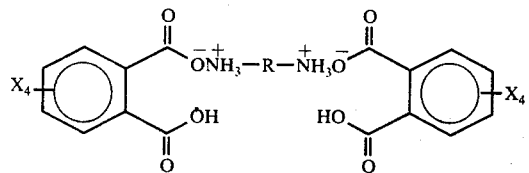

wherein X is halogen and R is an alkylene or cycloalkylene group containing 2-15 carbon atoms, and, when a bisimide is desired, (3) recovering the bis-tetrahalophthalate and (4) heating it at about 140°-300° C. until the acid number is substantially 0, indicating the formation of an N,N'-(cyclo)alkylene-bis tetrahalophthalimide corresponding to the formula:

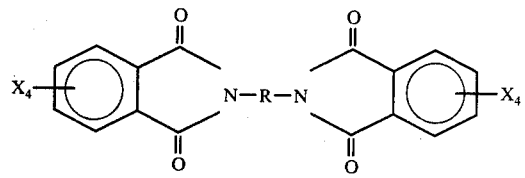

wherein X is halogen and R is an alkylene or cycloalkylene group containing 2-15 carbon atoms.

DESCRIPTION OF THE PREFERRED EMBODIMENTS

The tetrahalophthalic anhydride that is hydrolyzed in the practice of the invention is usually tetrabromophthalic anhydride, tetrachlorophthalic anhydride, or a mixture thereof; and it is preferably tetrabromophthalic anhydride.

As indicated above, the diaminoalkane or diaminocycloalkane that is used in the practice of the invention can be any such compound containing 2-15 carbon atoms. However, it is preferably a diaminoalkane containing 2-6 carbon atoms and most preferably 1,2-diaminoethane. Exemplary of other diamines that can be used are 1,2-diaminopropane, 1,3-diaminopropane, 1,4-diaminobutane, 1,5-diaminopentane, 1,6-diaminohexane, 1,2-diaminocyclohexane, 1,12-diaminododecane, 4,4'-methylene-bis-cyclohexylamine, etc.

The manner of hydrolyzing the anhydride is not critical except, of course, that water must be present to permit hydrolysis. The hydrolysis ca be conducted by conventional techniques. However, it is preferred to conduct the hydrolysis by sequentially treating an aqueous suspension of the anhydride with sodium hydroxide and hydrochloric acid or by hydrolyzing the anhydride in an aqueous medium containing 5-70%, preferably 10-50%, of an inert polar organic solvent, based on the weight of the total medium. Suitable polar organic solvents that are inert in the processes of the invention include, e.g., acetic, propionic, butyric, valeric, and other fatty acids containing 2-12 carbon atoms dioxane, etc.

The total amount of reaction medium employed for the hydrolysis, although not critical, is conveniently such as to provide a solids content of about 5-45%, preferably about 25-40%, by weight when the diamine is added for the subsequent step of the synthesis. The temperature used for the hydrolysis may be any conventional hydrolysis temperature but is preferably the same as the temperature that is to be used for the subsequent step of the synthesis, usually a temperature in the range of about 20°-200° C. Superatmospheric pressures are used at the higher reaction temperatures to prevent boiling.

The reaction of the diamine with the tetrahalophthalic acid is conducted on the reaction mixture resulting from the hydrolysis step but is not otherwise critical. Addition of the diamine may be delayed until the anhydride has been completely hydrolyzed to the acid, or it may be commenced when only a portion of the anhydride has been hydrolyzed. It has been found that reaction temperatures of about 25°–50° C. are particularly suitable when the NaOH/HCl hydrolysis technique has been used, and temperatures of about 90°–100° C. are most advantageously employed when the hydrolysis has been conducted in an aqueous medium containing an inert polar organic solvent. However, as indicated above, the reaction may be conducted at other temperatures, particularly temperatures in the range of about 20°–200° C., superatmospheric pressures being employable when they are desired to prevent boiling. It is also advantageous to conduct the reaction by adding the diamine gradually to the reaction mixture, e.g., over a period of about 0.25–4 hours, and then continuing to heat the reaction mixture for at least about 45 minutes, frequently for about 0.75–2 hours. The product may then be recovered by conventional cooling, filtering, and drying techniques.

When the alkylene- or cycloalkylenediammonium-bis-tetrahalophthalate thus obtained is desired only as an intermediate for the preparation of a bisimide, it may then be converted to the bisimide by heating it at about 140°–300° C. until the acid number is substantially 0. The time required for this reaction varies with the particular temperature employed but is usually in the range of about 1–48 hours, the shorter times being sufficient at the higher temperatures and the longer times sometimes being required at the lower temperatures.

The invention is advantageous in that it provides an economical and easily controlled process for preparing N,N'-(cyclo)-alkylene-bis-tetrahalophthalimides, which have known utility as flame retardants, and it is conducive to the formation of a readily filterable product. It is also advantageous in that the process leads to the formation of the bisimides via novel (cyclo)alkylenediammonium-bis-tetrahalophthalate intermediates which are useful per se as flame retardants. The following examples are given to illustrate the invention and are not intended as a limitation thereof.

EXAMPLE I

PART A

Charge 205 g. of water, 95.4 g. of acetic acid, and 99.3 g. of tetrabromophthalic anhydride to a suitable reaction vessel. Heat the mixture to 95° C., and add a solution of 6.45 g. of 1,2-diaminoethane in 18 g. of water over a period of 30 minutes. Continue heating the reaction mixture at 95°–100° C. for an additional hour. Then cool to 25° C., filter to separate the product, and dry the product in a vacuum oven at 100° C. for 17 hours. The process results in the formation of 103.4 g. of ethylenediammonium-bis-tetrabromophthalate, a white crystalline solid having a bromine content of 61.4%, compared with the 62.5% bromine content calculated for $C_{18}H_{12}N_2O_8$. Infra-red and thermogravimetric analyses support the identification of the product.

PART B

Heat the product of Part A in a vacuum oven at 150° C. for 17 hours. The process results in 100% conversion to N,N'-ethylene-bis-tetrabromophthalimide, a light yellow solid having an acid number of 0.05 and a melting point of 455°–457° C. Elemental, IR, and TGA analyses support the indentification of the product.

EXAMPLE II

Repeat Example I except for replacing the 1,2-diaminoethane with an equimolar amount of 1,2-diaminopropane and replacing the acetic acid with an equal weight of propionic acid in Part A and heating at 180° C. instead of 150° C. in Part B. The process of Part A results in the formation of a white crystalline solid which is identified as 1,2-propylenediammonium-bis-tetrabromophthalate by elemental, TGA, and IR analyses. The process of Part B results in the formation of N,N'-(1,2-propylene)-bis-tetrabromophthalimide, a light yellow solid having an acid number of 0.

EXAMPLE III

Repeat Example I except for replacing the 1,2-diaminoethane with an equimolar amount of 1,3-diaminopropane and replacing the acetic acid with an equal weight of propionic acid in Part A. The process of Part A results in the formation of a white crystalline solid which is identified as 1,3-propylenediammonium-bis-tetrabromophthalate by elemental, TGA, and IR analyses. The process of Part B results in the formation of N,N'-(1,3-propylene)-bis-tetrabromophthalimide, a light yellow solid having an acid number of 0 and a melting point of 329°–332° C.

EXAMPLE IV

PART A

Charge 800 ml. of water and 40 g. of sodium hydroxide to a suitable reaction vessel. Add 237 g. of tetrabromophthalic anhydride, and stir the mixture for 15 minutes. Add 83 ml. of concentreated hydrochloric acid over a period of one hour. Then add 30.4 g. of 1,6-diaminohexane to the resultant slurry over a period of 30 minutes. Stir the mixture for two hours at 25°–38° C. and filter to isolate 234.5 g. of hexamethylenediammonium-bis-tetrabromophthalate, a white solid. The identification of the compound is supported by elemental, TGA, and IR analyses.

PART B

Heat the product the Part A in a vacuum oven at 200° C. for one hour. The process results in the formation of 224 g. of N,N'-hexamethylene-bis-tetrabromophthalimide, a light yellow solid having an acid number of 0.6 and a melting point of 350°–355° C.

EXAMPLE V

Repeat Example I except for replacing 25% of the tetrabromophthalic anhydride with tetrachlorophthalic anhydride and replacing the acetic acid with an equal weight of propionic acid in Part A and heating for 48 hours in Part B. Analyses show that the process of Part A results in the formation of a mixture of ethylenediammonium-bis-tetrabromophthalate, ethylenediammonium-bis-tetrachlorophthalate, and ethylenediammonium tetrabromophthalate tetrachlorophthalate, and the process of Part B results in the formation of a mixture of N,N'-ethylene-bis-tetrabromophthalimide, N,N'-ethylene-XC -tetrachlorophthalimide, and N,N'-ethylene tetrabromophthalimide tetrachlorophthalimide.

EXAMPLE VI

Repeat Example V except for replacing another 25% of the tetrabromophthalic anhydride (i.e., 50% of the tetrabromophthalic anhydride of Example I) with tetrachlorophthalic anhydride. The products of Parts A and B are the same as in Example V except for containing higher percentages of ethylenediammonium-bis-tetrachlorophthalate in Part A and N,N'-ethylene-bis-tetrachlorophthalimide in Part B.

EXAMPLE VII

Repeat Example VI except for replacing the remainder of the tetrabromophthalic anhydride with tetrachlorophthalic anhydride. The process of Part A results in the formation of ethylenediammonium-bis-tetrachlorophthalate, and the process of Part B results in the formation of N,N'-ethylene-bis-tetrachlorophthalimide.

Similar results are observed when the examples are repeated except that one or more ingredients ae replaced by materials taught to be their equivalents in the specification.

It is obvious that many variations may be made in the products and processes set forth above without departing from the spirit and scope of this invention.

What is claimed is:

1. An alkylene- or cycloalkylenediammonium-bis-tetrahalophthalate corresponding to the formula:

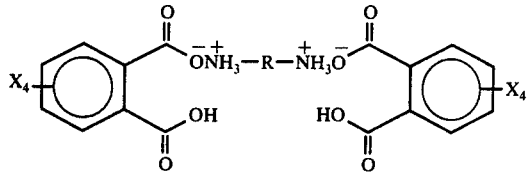

wherein X is halogen and R is an alkylene or cycloalkylene group containing 2–15 carbon atoms.

2. The bis-tetrahalophthalate of claim 1 wherein X is bromine.

3. The bis-tetrahalophthalate of claim 1 wherein X is chlorine.

4. The bis-tetrahalophthalate of claim 1 wherein R is a 1,2-ethylene group.

5. The bis-tetrahalophthalate of claim 1 wherein R is a 1,2-propylene group.

6. The bis-tetrahalophthalate of claim 1 wherein R is a 1,3-propylene group.

7. The bis-tetrahalophthalate of claim 1 wherein R is a 1,6-hexamethylene group.

8. The bis-tetrahalophthalate of claim 1 wherein R is a 1,2-ethylene group and X is bromine.

* * * * *